(12) United States Patent
Gough et al.

(10) Patent No.: US 7,871,456 B2
(45) Date of Patent: Jan. 18, 2011

(54) MEMBRANES WITH CONTROLLED PERMEABILITY TO POLAR AND APOLAR MOLECULES IN SOLUTION AND METHODS OF MAKING SAME

(75) Inventors: David A. Gough, Solana Beach, CA (US); Joseph Y. Lucisano, San Diego, CA (US); Joe T. Lin, San Diego, CA (US); Hwai-Min Tsay, San Diego, CA (US); Drahoslav Lim, San Diego, CA (US); Jana Limova, legal representative, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1009 days.

(21) Appl. No.: 11/503,461

(22) Filed: Aug. 10, 2006

(65) Prior Publication Data
US 2008/0034972 A1    Feb. 14, 2008

(51) Int. Cl.
*B01D 53/22* (2006.01)
*B01D 71/06* (2006.01)
*A61B 5/00* (2006.01)

(52) U.S. Cl. .................. 95/45; 95/46; 95/51; 96/4; 96/11; 96/12; 96/13; 96/14; 210/640; 210/500.27; 210/500.33; 600/347; 600/365; 204/403.05; 204/403.06; 204/418

(58) Field of Classification Search ................ 96/4, 96/11, 12, 13, 14; 95/45, 46, 51, 54; 210/640, 210/500.21, 500.27, 500.28, 500.33, 500.35; 600/345, 347, 365; 204/403.5, 403.6, 415, 204/418, 403.05, 403.06
See application file for complete search history.

(56) References Cited

U.S. PATENT DOCUMENTS

| 4,484,987 A | * | 11/1984 | Gough | 204/418 |
| 4,637,861 A | | 1/1987 | Krull et al. | 205/782.5 |
| 4,890,620 A | * | 1/1990 | Gough | 204/415 |
| 5,284,140 A | * | 2/1994 | Allen et al. | 204/415 |
| 5,322,063 A | | 6/1994 | Allen et al. | |

(Continued)

FOREIGN PATENT DOCUMENTS

WO    WO 92/13271    8/1992

OTHER PUBLICATIONS

Armour, J.C et al., "Application of a Chronic Intravascular Blood Glucose Sensor in Dogs", Diabetes 39 (1990), 1519-26.
Gough, D.A. et al., "A Novel Rotated Disc Electrode and Time Lag Method for Characterizing Mass Transport in Liquid-Membrane Systems", *Journal of the American Institute of Chemical Engineers* 26, 1013 (1980).

(Continued)

*Primary Examiner*—Jason M Greene
(74) *Attorney, Agent, or Firm*—DLA Piper LLP (US)

(57) ABSTRACT

A membrane for use in an implantable glucose sensor including at least one crosslinked substantially hydrophobic polymer and at least one crosslinked substantially hydrophilic polymer; wherein the first and second polymers are different polymers and substantially form an interpenetrating polymer network, semi-interpenetrating polymer network, polymer blend, or copolymer. The membranes are generally characterized by providing a permeability ratio of oxygen to glucose of about 1 to about 1000 in units of (mg/dl glucose) per (mmHg oxygen). Three methods of making membranes from hydrophobic and hydrophilic monomers formed into polymer networks are provided, wherein according to at least two of the methods, the monomers may be substantially immiscible with one another.

42 Claims, 4 Drawing Sheets

U.S. PATENT DOCUMENTS

| | | | |
|---|---|---|---|
| 5,431,160 A * | 7/1995 | Wilkins | 600/347 |
| 5,776,324 A * | 7/1998 | Usala | 600/345 |
| 5,777,060 A * | 7/1998 | Van Antwerp | 600/365 |
| 5,882,494 A | 3/1999 | Van Antwerp | |
| 6,081,736 A * | 6/2000 | Colvin et al. | 600/365 |
| 6,200,772 B1 | 3/2001 | Vadgama et al. | |
| 6,721,587 B2 | 4/2004 | Gough | |
| 7,146,203 B2 * | 12/2006 | Botvinick et al. | 600/345 |
| 2002/0123087 A1 | 9/2002 | Vachon et al. | |
| 2003/0217966 A1 * | 11/2003 | Tapsak et al. | 210/500.21 |
| 2004/0106857 A1 * | 6/2004 | Gough | 600/345 |
| 2006/0086624 A1 | 4/2006 | Tapsak et al. | 205/775 |
| 2008/0033269 A1 * | 2/2008 | Zhang | 600/347 |

OTHER PUBLICATIONS

Gough, D.A. et al., "Membrane-Covered, Rotated Disc Electrode," *Anal. Chem.* 51 (1979), 439-44.

Leypoldt J.K. et al., "Model of a Two-Substrate Enzyme Electrode for Glucose", *Analytical Chemistry*, 56, 2896 (1984).

Leypoldt J.K. et al., "Diffusion and the Limiting Substrate in Two-Substrate Immobilized Enzyme Systems", *Biotechnology and Bioengineering*, XXIV, 2705 (1982).

Makale, et al., "Tissue window chamber system for validation of implanted oxygen sensors," Am J Physiol Heart Circ Physiol, Jun. 2003; 284: 2288-2294.

* cited by examiner

MEMBRANES WITH CONTROLLED PERMEABILITY TO POLAR AND APOLAR MOLECULES IN SOLUTION AND METHODS OF MAKING SAME

STATEMENT OF GOVERNMENT SUPPORT

This invention was made with government support under Grant Number DK55064 awarded by the National Institutes of Health. The government has certain rights in the invention.

FIELD OF THE INVENTION

This disclosure broadly relates to, among other things, biocompatible synthetic membranes comprising intimately associated polymer networks that can provide controlled permeability for polar and apolar molecules and methods for synthesis of these membranes.

BACKGROUND OF THE INVENTION

A number of medical devices that function as implants in the body require a supply or flux of specific biochemicals from the tissue surrounding them for their function. One example of such a device is a type of implanted biochemical-specific sensor known as the "enzyme electrode," which is used to monitor the bodily concentration of key metabolites such as glucose, lactate, and pyruvate. Information about the concentration of such metabolites can be of benefit in devising therapies for diseases in which these metabolites may play important roles. Certain sensors for these metabolites function on the basis of a chemical reaction between the dissolved, polar molecule of interest and the apolar molecule oxygen, which polar and apolar molecules are supplied as fluxes from the bodily tissues surrounding the implant into a reaction zone within the implant. A chemical product of this reaction or unconsumed oxygen itself can be detected electrochemically to provide an indication of the concentration of the metabolite of interest.

A limitation to the use of such implanted biosensors is that the concentrations of the metabolites of interest are typically substantially higher than the concentration of the oxygen coreactant. For example, the typical concentration of glucose in the blood is about 4 to about 20 mM, whereas a typical concentration of oxygen in blood plasma may be only about 0.05 to about 0.1 mM. Oxygen concentrations in other tissue fluids may be even lower. As the chemical reaction, and thus, the sensor signal, is limited by the reactant that is present in the sensor's reaction zone at lowest concentration, an implanted sensor of simple construction would remain limited by oxygen and would therefore be insensitive to the metabolite of interest. There is, therefore, a need for differential control of the permeability of the sensor membrane to restrict or modulate the flux of the metabolite of interest and provide a stoichiometric equivalent or excess of oxygen in the reaction zone. The sensor incorporating a membrane can then be sensitive to the metabolite of interest over the physiologic range. Also, for successful function of the implanted medical device, the membrane material exposed to the bodily tissue must further be biocompatible, or elicit a favorable response from the body.

Another example of the application of biocompatible membranes with controlled differential permeability is in encapsulation of living tissues, cells, cell derivations, or other biochemically-active constructs used in implant devices to restore biological function that has been lost or compromised due to disease or accident. An example is the isolation and encapsulation of functional Islets of Langerhans from the pancreas of healthy human or cross-species donors or cadavers, or similar cells derived from cultures for implantation in individuals with diabetes. An important purpose of the membrane in this application is to allow diffusional access of oxygen, glucose and nutrients from tissues of the recipient. In order to achieve optimal function of the implanted tissue and avoid toxicity due to substrate imbalances, differential control of membrane permeability is of great importance. By limiting the ingress of potentially damaging cells or molecules or by limiting the egress of cytokines or other molecules that could trigger a response from the host, the membrane can also provide protection against immunological or other biochemically-mediated attack.

Other applications where differential control of permeability is advantageous include: bioreactors containing enzymes, cells, or living tissues; membranes of artificial kidney devices that function by differential removal of metabolic waste products from blood or biological fluids; membranes of artificial respiratory devices that function by controlling the gas content of blood or biological fluids; and various implanted drug delivery devices. In these cases, differential control of membrane permeability can substantially enhance the function of the device.

SUMMARY OF THE INVENTION

The invention provides biocompatible membranes having differential control of permeability for polar molecules such as glucose and apolar molecules such as oxygen and devices and applications thereof. The membrane can be composed of intimately associated hydrophobic and hydrophilic polymers that provide permeability for apolar and polar solutes, respectively. In the membrane, the intimate association of the hydrophobic and hydrophilic polymers may be of the form commonly referred to as interpenetrating polymer networks (IPNs), semi-interpenetrating polymer networks (SIPNs), or polymer blends. The IUPAC definitions of IPNs, SIPNs, and polymer blends provided in *The Compendium of Chemical Terminology, The Gold Book*, $2^{nd}$ Edition, A. D. McNaught and A. Wilkinson, eds., Blackwell Science, 1997 are incorporated herein by reference. In accord with such definitions, two or more networks are interpenetrating if they cannot be separated without breaking chemical bonds, whereas networks that are separable, in principle, without breaking chemical bonds are defined as semi-interpenetrating polymer networks, a type of polymer blend, which more broadly includes any mixture of polymers that is macroscopically homogeneous. Permeabilities to polar and apolar solutes can be predictable and controllable over useful ranges by adjustments of the ratios of monomers used in preparation of the polymer membranes. Further, the membrane can be prepared with starting materials known to produce biocompatible polymers, and has been shown to be biocompatible by toxicity testing in tissue culture and by histologic analysis of tissues surrounding implanted devices containing the membrane material. To these ends, methods for manufacturing the membranes of the invention are also provided.

The invention provides membranes comprising a first polymer and a second polymer. The first and second polymers are different polymers that may or may not be crosslinked to themselves, or to each other, or to an additional polymer or polymers in the membrane. The first polymer is substantially hydrophobic and the second polymer is substantially hydrophilic, and the membrane may be characterized by its ratio of oxygen to glucose permeability. Such permeability ratio can be expressed as the maximum detectable ratio of glucose to oxygen concentration of an enzymatic glucose sensor, when the membrane is incorporated in such a sensor, where such a sensor is based on the detection of oxygen unconsumed by the enzyme reaction, and after taking into account the effects of external mass transfer conditions and the enzyme reaction stoichiometry. It is important to note that, while this measure of permeability ratio is directly related to the performance of the membrane when it is incorporated into an oxygen-detecting enzyme electrode, the membranes of the invention may also be utilized to advantage in other types of enzyme electrodes, for instance those that are based on the detection of hydrogen peroxide. Characterization of membrane permeability ratio (which is an intrinsic material property) in terms of performance in oxygen-detecting enzyme electrodes is utilized for convenience, but in no manner limits the application of the invention in enzyme electrodes to only the oxygen-detecting type. Detailed discussions of the relationship between membrane permeability ratio and the maximum detectable ratio of glucose to oxygen concentration of oxygen-detecting, enzymatic, membrane-based sensors are provided in "Model of a Two-Substrate Enzyme Electrode for Glucose," J. K. Leypoldt and D. A. Gough, *Analytical Chemistry*, 56, 2896 (1984) and "Diffusion and the Limiting Substrate in Two-Substrate Immobilized Enzyme Systems," J. K. Leypoldt and D. A. Gough, *Biotechnology and Bioengineering*, XXIV, 2705 (1982), incorporated herein by reference. The membranes of the invention are characterized by a permeability ratio of oxygen to glucose of about 1 to about 100 in units of (mg/dl glucose) per (mmHg oxygen). Note that while this measure of permeability ratio utilizes units of a glucose concentration to an oxygen concentration, it is nevertheless a measure of the ratio of oxygen to glucose permeability of the membrane.

Alternatively, the membrane may be characterized by its ratio of permeabilities of oxygen to hydroquinone (a polar molecule), such permeabilities determined using a membrane-covered rotating disk electrode (MCRDE), such as that described in "A Novel Rotated Disc Electrode and Time Lag Method for Characterizing Mass Transport in Liquid-Membrane Systems," D. A. Gough and J. K. Leypoldt, *Journal of the American Institute of Chemical Engineers* 26, 1013 (1980). Additionally, the membranes may be characterized by their water content, expressed as a percentage of the wet membrane weight. For a given polymer system, the permeability of the membrane to polar molecules can be related in a useful manner to such water content.

In one preferred embodiment, the membranes of the invention consist of hydrophobic poly(dimethylsiloxane) (or PDMS) or other silicon-containing polymers, and substantially hydrophilic poly(2-hydroxyethylmethacrylate) (or HEMA) or other hydrophilic acrylate-containing polymers. These polymers are not typically mutually soluble in common solvents or in each other, and their precursor monomeric forms are not directly miscible. These incompatibilities present a fundamental difficulty in preparing interpenetrating networks of these polymers. The invention therefore provides methods for producing suitable membranes incorporating IPNs and SIPNs of the polymers.

In one embodiment of the manufacturing methods of the invention, a silylated hydrophilic monomer is provided, either alone, or combined in a mixture with a hydrophobic monomer. The silylated hydrophilic monomer or monomer mixture is impregnated into a hydrophobic polymeric structure, then the monomers are polymerized, networks of the polymers are formed (such as IPNs or SIPNs), and then the polymerized silylated hydrophilic monomer is desilylated.

In another embodiment of the manufacturing methods of the invention, a mixture of a silylated hydrophilic monomer and a hydrophobic monomer is provided. The mixture is placed in a cavity, such as a membrane mold, the monomers are polymerized and cross-linked (to form IPNs or SIPNs), and then the polymerized sylilated hydrophilic monomer is desilylated.

In yet a further embodiment of the manufacturing methods of the invention, membranes are prepared by co-polymerizing non-silylated hydrophobic and hydrophilic monomers in a mutually compatible solvent system.

Also provided by the invention is a multi-component membrane assembly, in which a membrane of the invention is operatively coupled to a consumptive layer containing enzymes and optionally coupled to one or more protective layers. Such protective layers are designed to protect either the membrane itself or underlying structures from components of environmental fluids or products of reactions in the consumptive layer. Such membrane assemblies may be used to advantage in the construction of sensors.

Also provided by the invention are glucose sensors, in which a membrane of the invention is mounted on a sensor body. To foster integration into bodily tissues, the surface texture of the membrane may be modified; e.g., by laser etching of the surface of the mold that is used to produce the membrane. The glucose sensors of the invention are biocompatible and well tolerated for implantation use in a body. Methods for use of the sensors to detect glucose levels in a body are also described.

Also provided by the invention are implantable devices including membranes of the invention, wherein the supply of substances by body tissues to the device or the supply of substances by the device to body tissues is modulated or controlled by diffusional properties of the described membranes.

For assessment of the properties of a membrane produced according to the invention, means for characterization of the membrane permeability using a membrane-covered rotated disc electrode (MCRDE) and additional means for assessing other membrane properties are also provided.

DETAILED DESCRIPTION OF THE INVENTION

A. Abbreviations Used in the Disclosure

Figure 1:
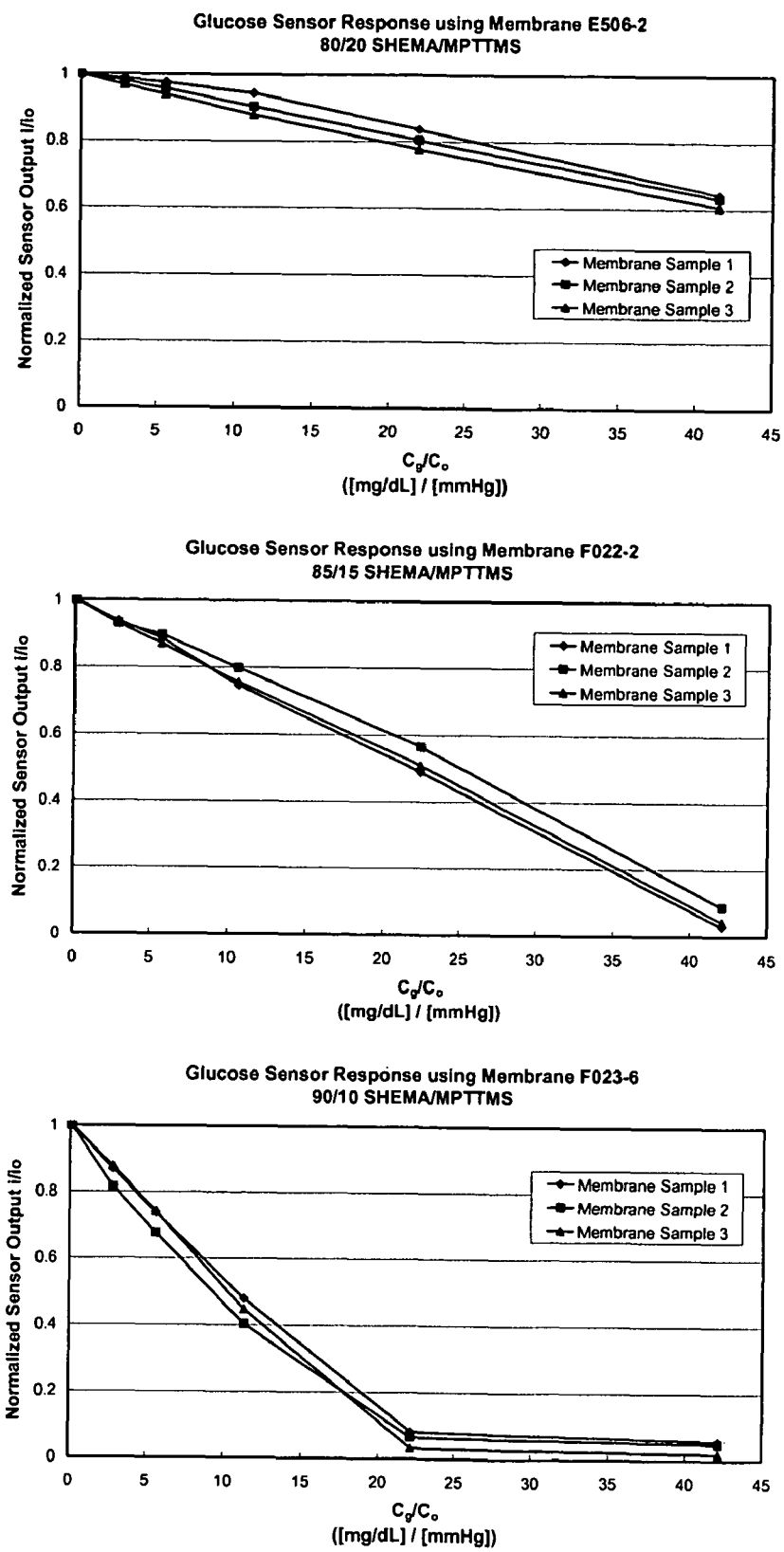
FIG. 1 illustrates normalized responses obtained in vitro from glucose sensors based on oxygen detection, in which membranes of the invention are mounted on sensor bodies and the sensors are subjected to stepwise additions of glucose at controlled oxygen concentration.

For ease of reference, the following abbreviations are used in the following disclosure. The abbreviations and definitions provided shall not limit the scope of the invention, which is defined by the appended claims:

AA: Allyl alcohol, a solvent and chain growth inhibitor

CPT: Cyclopentanone, a solvent

EGDMA: Ethylene glycol dimethacylate, a crosslinking agent

ESP28: Esperox 28™ (Crompton Corporation), tertiary-butyl peroxy 2-ethyl hexanoate; an organic peroxide, an initiator ESP33: Esperox 33M™ (Crompton Corporation), tertiary-butyl peroxyneodecanoate, 75% in mineral spirits; an organic peroxide, an initiator HEMA: 2-hydroxyethylmethacrylate, a hydrophilic monomer HPMA: 3-hydroxypropylmethacrylate, a hydrophilic monomer IPNs: Interpenetrating polymer networks IUPAC: International Union of Pure and Applied Chemistry MCRDE: Membrane-covered, rotated disc electrode system used for characterization of membrane permeability to specific solutes MEK: Methyl ethyl ketone, a solvent Membrane: A polymer, or polymer-containing structure, wherein the polymer has specific, controlled permeabilities to polar and non-polar species mg/dl: milligrams per deciliter (unit of concentration)

mmHg: millimeters of mercury (unit of partial pressure)

MPPMDS: 3-methacryloxypropylpentamethyl disiloxane, a hydrophobic monomer

MPTTMS: 3-methacryloxypropyl tris(trimethylsil)oxy silane, a hydrophobic monomer PBS: Phosphate-buffered saline solution (0.1 Molar sodium chloride, 0.01 Molar potassium phosphates, pH7.4)

PDMS: poly(dimethylsiloxane), also known as silicone rubber, a hydrophobic polymer S-HEMA: trimethylsiloxyethyl methacrylate, a monomer produced by silylation of HEMA SIPNs: Semi-interpenetrating polymer networks TFEMA: trifluoroethyl methacrylate, a hydrophobic monomer.

B. General Characteristics of the Membranes of the Invention

The manufacturing methods of the invention produce membranes of three structural types. Therefore, membranes of the invention are referred to in this disclosure as Type 1, Type 2 and Type 3 membranes.

For Type 1 membranes, starting materials include a hydrophobic polymer, a hydrophilic monomer, and (optionally) a hydrophobic monomer (or pre-polymer). The hydrophilic monomer is modified by masking its polar groups to enhance miscibility with the optional hydrophobic monomer and solubility in the hydrophobic polymer, into which the masked hydrophilic monomer or a mixture of the masked hydrophilic monomer and the hydrophobic monomer is impregnated. After admixture, impregnation, and co-polymerization, the resulting masked hydrophilic polymer is unmasked, restoring hydrophilicity to the polymer. Type 2 membranes require only the masked hydrophilic monomer and the hydrophobic monomer. For Type 3 membranes, the hydrophilic monomer starting material is not masked, but rather it is co-polymerized with a hydrophobic monomer in a mutually compatible solvent system. The manufacturing methods described therefore differ in certain respects. However, all of the membranes of the invention share some common characteristics, as described below.

1. Properties of Suitable First and Second Membrane Polymers.

The membranes of the invention all include a first polymer and a second polymer that do not generally share the same solubility properties in their uncrosslinked forms in that the first polymer is substantially hydrophobic and the second polymer is substantially hydrophilic. For example, the first polymer can be soluble in hexane but insoluble in water or a water-alcohol mixture, whereas the second polymer can be soluble in water or a water-alcohol mixture but insoluble in hexane. Type 1 membranes may also include an additional hydrophobic polymer.

Preferred monomeric starting materials and polymers produced therefrom for use in membranes of the invention are noted with respect to each type of membrane described herein. Those of ordinary skill in the art will recognize that monomeric starting materials and polymer end-products other than those explicitly identified as being preferred may be utilized in the invention, and that the manufacturing methods in particular are susceptible to use with a wide variety of hydrophobic and hydrophilic monomers for polymerization into membrane polymers.

The invention is susceptible to use with numerous different kinds of synthetic polymers. Particular materials whose properties (e.g., of biocompatibility and tolerance to implantation) are especially well suited to use in the invention are noted in the disclosure. However, those of ordinary skill in the art will recognize that other polymers may potentially be utilized as well. For example, membrane polymers are well-known in the art and can be purely synthetic, natural, or modified natural polymers. Porosity of the membrane can be varied from non-porous to porous. Examples of membrane materials generally include polyethylene, polyvinyl chloride, polytetrafluoroethylene, polypropylene, cellophane, modified cellulose, cuprophane, polyacrylamide, cellulose acetate, polymethyl methacrylate, silicones, polycarbonate, polysulfone, nylons, and collagen. Synthetic polymers generally include those described in, for example, (1) *Concise Encyclopedia of polymer Science and Engineering*, J. Kroschwitz (Ex. Ed.), John Wiley, 1990; (2) *Contemporary Polymer Chemistry*, H. R. Allcock, F. W. Lampe, Prentice-Hall, 1981; (3) *Textbook of Polymer Science, 3$^{rd}$ Ed.*, F. Billmeyer, John Wiley, 1984; and (4) *Surface and Interfacial Aspects of Biomedical Polymers, Vol. 1, Surface Chemistry and Physics*, Ed. J. Andrade, Plenum, 1985.

The first polymer is a substantially hydrophobic polymer, wherein the polymer chains may be cross-linked to one another. The polymer chains can be crosslinked with themselves. Crosslinking can be chemical or physical. Crosslinking can result in the polymer being swellable in solvents but not soluble. Hydrophobic polymers can comprise sufficient amounts of non-polar components so that water tends to bead up on the polymer rather than spread out, indicating surface hydrophobicity. For example, the contact angle of water on the polymer surface can be at least 90°, more particularly, at least 95°, more particularly, at least 100°, or more particularly, at least 105°. The polymer can provide a stable, substantially hydrophobic surface structure even if the bulk polymer structure and the surface polymer structure are not the same. Contact angle measurements and surface structure dynamics for polymer surfaces are described in, for example, the Andrade text noted above including, for example, Chapter 2 ("Polymer Surface Dynamics") and Chapter 7 ("The Contact Angle and Interface Energetics").

The structure of the first polymer is not particularly limited as long as it is substantially hydrophobic and possesses sufficient permeability to apolar molecules of interest for the intended application. Also, the biocompatibility must be good enough for the particular application. The degree of crosslinking can be varied for a particular application in which the membrane is to be used (e.g., an implantable glucose sensor). The polymer in general should have a structure so that if it is prepared without crosslinking it is soluble in organic solvents but not soluble in water.

The hydrophobicity can be generated from the polymer side groups, polymer end groups, or the polymer backbone, although the polymer backbone tends to be shielded by the side and end groups. In general, groups which can impart hydrophobicity include, for example, methyl, ethyl, propyl, n-alkyl, linear alkyl, branched alkyl, C1-C18 groups, C1-C12 groups, and more generally alkyl; aryl and aromatic groups; and fluorinated and perfluorinated groups including fluoroalkyl and fluoroaryl groups.

Different polymer architectures can be used. The polymer can be a homopolymer, a copolymer, a terpolymer, a block copolymer, a linear polymer, a graft copolymer, and the like. The polymer can be an addition polymer or a condensation polymer or a polymer prepared by ring-opening polymerization.

The first polymer can also be an elastomer. It can have a glass transition temperature below about 25° C., or below about 0° C., or below about −25° C., or below about −50° C.

Before crosslinking, the first polymer can have a weight average molecular weight of at least about 1,000, or at least about 5,000, or at least about 10,000, or at least about 20,000.

The first polymer can be synthesized directly or it can be purchased commercially. Polymer purchased commercially can be purified by, for example, extraction before use.

The first polymer can, for example, be a siloxane, polycarbonate, polyphosphazene, cellulose acetate or other hydrophobically-modified cellulose, with silicones being especially preferred for their known properties of biocompatibility and good track record for use in implantable devices.

For use in the preferred membranes of the invention (versus general use in the manufacturing methods), the first polymer should preferably be a non-polyurethane, a non-polyurea, or a non-polyurethaneurea, and so will preferably not include polysiloxane polyurea such as those used in biosensors in US Patent Publication 2002/0123087 to Vachon et al., or polyurethane ureas such as described in US Patent Publication 2003/0217966 to Tapsak et al., U.S. Pat. No. 6,200,772 to Vadgama et al.; U.S. Pat. No. 5,322,063 to Allen et al.; WO 92/13271 to Rhodes et al.; U.S. Pat. Nos. 5,882,494 and 5,777,060 to Van Antwerp.

The first polymer can comprise siloxane linkages in the polymer backbone including polyorganosiloxanes or poly (dimethyl siloxane) or silicone rubber or silicone elastomer. Silicones are well-known in the art and are described, for example, in the *Concise Encyclopedia* noted above under "Silicones," the disclosure of which is incorporated herein by this reference to illustrate knowledge in the art regarding biocompatible silicones.

For example, siloxane polymers useful in the invention can be represented as —[OSiR$_1$R$_2$]$_x$— wherein R$_1$ and R$_2$ independently of each other can be, for example, hydrogen, optionally substituted alkyl, alkenyl, alkynyl, aryl, haloalkyl, haloakenyl, haloalkynyl, haloaryl, heterocyclyl, and haloheterocyclyl.

The second polymer is a substantially hydrophilic polymer, wherein the polymer chains can be crosslinked with themselves. Crosslinking can be chemical or physical. Crosslinking can result in the polymer being swellable in solvents but not soluble. Hydrophilic polymers can comprise sufficient amounts of polar components so that water tends to not bead up on the polymer but rather spreads out. For example, the contact angle of water on the polymer surface can be less than 90°, more particularly, less than 80°, more particularly, less than 70°, or more particularly, less than 60°. The polymer can provide a stable, substantially hydrophilic surface structure even if the bulk polymer structure and the surface polymer structure are not the same. Contact angle measurements and surface structure dynamics for polymer surfaces are described in, for example, the Andrade text noted above including, for example, Chapter 2 ("Polymer Surface Dynamics") and Chapter 7 ("The Contact Angle and Interface Energetics").

The structure of the second polymer is not particularly limited as long as it is substantially hydrophilic. Also, the biocompatibility must be good enough for the particular application. The degree of crosslinking can be varied for a particular application. The polymer in general should have a structure so that if it is prepared without crosslinking it is soluble or swellable in water and polar solvents but not soluble or swellable in non-polar solvents such as, for example, hexane.

The hydrophilicity can be generated from the polymer side groups, polymer end groups, or the polymer backbone, although the polymer backbone tends to be shielded by the side and end groups. In general, groups which can impart hydrophilicity are well known in the art and include polar groups, for example, derivatized methyl, ethyl, propyl, n-alkyl, linear alkyl, branched alkyl, C1-C18 groups, C1-C12 groups, and more generally alkyl; aryl and aromatic groups, all derivatized with hydrophilic moieties such as hydroxyl or amino groups. Other methods for imparting hydrophilicity include treatment of polymer with a di-C$_{10-12}$ fatty acid ester of polyethylene glycol or other wettability enhancers.

Different polymer architectures can be used. The polymer can be a homopolymer, a copolymer, a terpolymer, a block copolymer, a linear polymer, a graft copolymer, and the like. The polymer can be an addition polymer or a condensation polymer or a polymer prepared by ring-opening polymerization.

The second polymer can also be an elastomer. It can have a glass transition temperature below about 25° C., or below about 0° C., or below about −25° C., or below about −50° C.

Before crosslinking, the second polymer can have a weight average molecular weight of at least about 1,000, or at least about 5,000, or at least about 10,000, or at least about 20,000.

In the methods of the invention; the second polymer is synthesized from a masked monomer (Type 1 or Type 2 membranes) or an unmasked monomer (Type 3 membrane).

The second polymer can be a water-soluble polymer which is crosslinked so that it is water-swellable such as a vinyl polymer, a polyether, polyester, polyamide, polyethylene oxide, polyvinyl pyrrolidone, polyvinyl alcohol, glutaraldehyde crosslinked proteins, collagen, albumin, alginates, and functionalized inorganic polymers such as functionalized siloxane or polyphosphazene.

For use in the membranes of the invention (versus manufacturing methods), the second polymer will preferably be a non-polyurethane, a non-polyurea, or a non-polyurethaneurea polymer. The second polymer will preferably include acrylate linkages in the polymer backbone and may also include hydrophilic derivatives of poly(acrylates) such as poly(hydroxyethyl methacrylate). Acrylates, methacrylates, or (meth)acrylates are well-known in the art and are described, for example, in the *Concise Encyclopedia* noted above under "Acrylic and Methacrylic Acid Polymers," the disclosure of which is incorporated herein by this reference to illustrate knowledge in the art regarding acrylate-linked polymers.

Because the second polymer is substantially hydrophilic (i.e., either entirely hydrophilic or optionally containing a hydrophobic component), it will not generally be readily miscible with the first, hydrophobic polymer. The hydrophilic monomer utilized to make the hydrophilic polymer in Type 1 and Type 2 membranes is therefore masked during polymerization with masking groups which temporarily make the monomer hydrophobic during polymerization but which are removed after polymerization so the original hydrophilicity is restored in the polymer. Such masking groups include derivatizing agents (often used to mask polar groups for gas chromatography analysis), with silylating agents (such as the trimethylsilyls) being preferred, although acylating agents (such as fluorinated anhydrides and fluoracylimidazoles) may be used to mask highly polar compounds, and alkylating agents (such as dialkylacetals) may be used for acidic polar compounds.

3. Interpenetrating and Semi-Interpenetrating Polymer Networks.

The membranes of the invention all preferably comprise IPNs or SIPNs composed of a first and second polymer. The general characteristics of IPNs and SIPNs are known in the art, as referenced above. IPNs comprise two or more polymers, each in network form, that cannot be separated without breaking chemical bonds, whereas SIPNs comprise two or more polymer networks that are separable, in principle, without breaking chemical bonds. In one type of IPN or SIPN ("sequential IPN" or "sequential SIPN"), a first polymer is crosslinked to form a network. Then a second polymer is formed and crosslinked directly in the presence of the first polymer. In a second type ("simultaneous IPN" or "simultaneous SIPN"), a mutual solution of monomers is prepared with respective crosslinkers which are then polymerized simultaneously in non-interfering mode. In a third type ("mixture IPN" or "mixture SIPN"), two lattices of linear polymers are mixed and simultaneously crosslinked. IPNs can swell but not dissolve in solvents, and creep and flow can be suppressed.

In an IPN, the first polymer can be crosslinked with itself using its specific crosslinker, and the second polymer can be crosslinked with itself using its respective crosslinker. In addition, some small amounts of reaction or crosslinking between the two polymers can be present when one crosslinker is capable of crosslinking both polymers, to form a block copolymer.

It will be appreciated that the first and second polymers need not necessarily be formed into full networks. If only the first polymer comprises a network and the second polymer is a linear chain or linear branching polymer, then a SIPN may be formed. The invention may therefore comprise either an IPN or a SIPN. Portions of the membrane monomers may also polymerize to form block polymers.

4. Continuity of Hydrophilic Channels.

Whatever the structural relationship of the first and second polymers in the membrane, there should be continuity between hydrophilic channels extending from one side of the membrane to the other to allow transport of polar molecules through the membrane. The continuity of hydrophilic channels across the membrane can result from the overlap or close approximation of hydrophilic polymer chains, and does not require a single, continuous hydrophilic polymer molecule to span the entire membrane thickness. Transport across the membrane of apolar molecules, which is enhanced by the presence of hydrophobic channels, does not require such channels to be continuous, since the apolar molecule can dissolve in, and diffuse through, the hydrophilic elements of the membrane as well.

5. Polymerization Initiators.

If desired, polymerization initiator compounds can be used. If desired, two such compounds may be used, a first one that is activated at a first temperature, and a second one that is activated at a second temperature. The total amount of initiator used in polymerization can be, for example, about 1 mass percent to about 5 mass percent, or about 1 mass percent to about 2 mass percent. The amount of the first and second initiator can be about the same, or one amount being within about 25% of the other amount.

6. Membrane Thicknesses.

The thickness of the membrane product is not particularly limited, as long as desired permeability properties are achieved. If the membrane is to be utilized in a biosensor, particular requirements for sensor time response characteristics may limit the allowable membrane thickness, since thicker membranes will extend the times required to reach a new diffusional steady-state during substrate concentration transients. The membrane thickness, without swelling, can be, for example, about 1 micron to about 1000 microns, or more particularly, about 10 microns to about 500 microns, or more particularly, about 25 microns to about 250 microns, or more particularly about 25 microns to about 75 microns. Very thin membrane layers, particularly those less than about 10 microns, may require mechanical support to be provided in the form of a backing membrane, which may be a porous, relatively inert structure.

7. Membrane Porosities.

The membranes can be non-porous, where transport of polar and apolar molecules across the membrane occurs primarily by diffusion. Porous membranes, where molecular transport properties are dominated by the geometry of physical pores, and such transport properties are relatively independent of the polymer properties per se, are outside the scope of this invention.

8. Permeability Ratios.

The membranes can be characterized by a permeability ratio of oxygen to glucose in units of (mg/dl glucose) per (mmHg oxygen). This ratio can be, for example, about 1 to about 1000, or more particularly, about 1 to about 100, or more particularly, about 10 to about 60. Alternatively, the membranes may be characterized by a permeability ratio of oxygen to hydroquinone of 100 to 10,000 (dimensionless).

9. Water Uptake Measurements.

The membranes can be soaked in and saturated with PBS and equilibrium water content measured. The water content can be, for example, about 1 wt. % to about 50 wt. %, and more particularly, about 1 wt. % to about 20 wt. %, or more particularly, about 5 wt. % to about 20 wt. %, or more particularly, about 5 wt. % to about 15 wt. %, or more particularly, about 10 wt. % to about 15 wt. %.

C. Methods of Making Type 1 Membranes of the Invention

Generally, Type 1 membranes are produced by impregnation of a hydrophobic polymer with a masked hydrophilic monomer, or a mixture of a masked hydrophilic monomer and a hydrophobic monomer, followed by polymerization and unmasking of the resulting hydrophilic polymer.

1. Type 1 Membrane-Specific Characteristics.

In a Type 1 membrane, the membrane can comprise: at least one first polymer which is a crosslinked substantially hydrophobic polymer, at least one second polymer which is a crosslinked substantially hydrophilic polymer, and optionally a third polymer which is a crosslinked hydrophobic polymer. For the latter, any hydrophobic polymer, such as those described herein for use as the first polymer, may be used. The first and second polymers are different polymers, whereas the third polymer may be of the same type as the first polymer, but is synthesized from a monomeric or pre-polymer form during production of the membrane.

The first polymer is provided in a solid form. The second, and, if included, third polymers, are synthesized by polymerization from monomers in the presence of the first polymer to substantially form an interpenetrating polymer network. Generally, Type 1 membranes are characterized by a permeability ratio of oxygen to glucose of about 1 to about 100 in units of (mg/dl glucose) per (mmHg oxygen).

The amounts of the first, second, and third polymers present in a Type 1 membrane are not particularly limited so long as the desired permeabilities to polar and apolar compounds can be achieved for a given application. The amount of the first polymer can be, for example, about 2 wt. % to about 75 wt. %, and more particularly the amount can be about 5 wt. % to about 30 wt. %, and more particularly, about 7 wt. % to about 20 wt. %, with respect to the total polymer content of the membrane including the first, second, and (if present) third polymers.

The amount of the second polymer can be, for example, about 25 wt. % to about 98 wt. %, and more particularly the amount can be about 70 wt. % to about 95 wt. %, and more particularly, about 80 wt. % to about 93 wt. %, with respect to the total polymer content of the membrane including the first, second, and (if present) third polymers.

2. Methods for Production of Type 1 Membranes.

To illustrate synthesis of Type 1 membranes, the practice of a manufacturing method of the invention for their production is exemplified below. The particular approach taken involved imbibing S-HEMA or a mixture of S-HEMA and MPTTMS into a solvent-extracted PDMS membrane, followed by formation of an interpenetrating silylated polymer from the impregnated monomer or monomers, and hydrophilization of the interpenetrating polymer by cleavage of the silyl groups. Adjustment of membrane permeability by variation of the formulation and characterization of the membrane permeability by use of a MCRDE are also exemplified.

S-HEMA was synthesized from the quantitative reaction of chlorotrimethylsilane and HEMA by methods known to those familiar with the art. A sheet of medical grade PDMS, dimensions 4×4 cm² in area, was soaked for 24 hours at room temperature in 30 ml of chloroform in a covered glass petri dish to cause equilibrium solvent swelling of the sheet. Sheet thicknesses (unswelled) ranged from 0.050 mm to 0.125 mm, with 0.05 mm being most preferred. The chloroform, which contained small amounts of extractables, was discarded and the sheet rinsed in pure chloroform. Residual chloroform in the sheet was then allowed to evaporate to dryness, causing a return of the sheet to near the original dimensions. The sheet was then placed in covered glass petri dish containing 30 ml of a four-component reactive cocktail in specified ratios including two monomers, S-HEMA and MPTTMS, a crosslinking agent EGDMA, and initiators ESP28 and ESP33. The amounts used of EGDMA ranged from about 1% to about 3% of the imbibing mixture, with 2% being the most preferred. The amounts used of ESP28 and ESP33 each ranged from about 1% to about 2% of the imbibing mixture, with 1.5% being the most preferred. The PDMS sheet was allowed to soak for 24 hours, causing it to imbibe the reactants.

Different sheets were prepared in this manner, wherein the ratio of S-HEMA to MPTTMS was varied from 100:0 to 60:40, with 95:5, 90:10 and 85:15 being the most preferred ratios. After imbibing the reactant mixture, each sheet was secured between glass plates and then heated in an oven at 90° C. for four hours followed by 110° C. for three hours to complete the polymerization of the imbibed monomers. Each sheet was then soaked at room temperature for various periods in dilute acetic acid (concentration ranged from 7% to 14%, with 7% being most preferred) to cause desilylation. The soaking periods were 3 to 14 days dependent on sheet thickness, with 7 days being the most preferred period. The acetic acid soak was followed by soaking for a minimum of three days in sodium bicarbonate solution (5% in water) to neutralize the acid and then soaking in several changes of PBS. Completion of these steps produced a hydrophilic membrane with predictable properties, based upon the formulation of the imbibing reactant mixture.

Membrane permeability to representative solutes was characterized using the MCRDE. Membrane discs 1 cm in diameter were cut from the membrane sheet and mounted onto a rotated disc electrode apparatus described by Gough, D. A. and J. K. Leypoldt, ("Membrane-Covered, Rotated Disc Electrode," *Anal. Chem.* 51 (1979), 439-44). The MCRDE was used with a thermostatted vessel maintained at 37° C. containing PBS. Oxygen and hydroquinone were employed as molecular diffusants for characterization of membrane permeability. Hydroquinone was used as a surrogate for glucose, as glucose undergoes a less reproducible electrochemical reaction at the electrode. Hydroquinone has similar molecular weight and dimensions to glucose, but reacts quantitatively at the electrode surface. The solution in the reaction vessel was either equilibrated with atmospheric oxygen at 0.22 mM or contained hydroquinone at 34.27 mM.

Measurements of the electrode current, which relate directly to the solute flux, were made at several electrode rotation rates. Plots were made of inverse diffusion current versus inverse square root of electrode rotation rate, in which the intercept on the vertical axis represents the limit where fluid mass-transfer resistance is negligible and membrane mass-transfer resistance is limiting. Membrane permeability was calculated from the inverse of the membrane mass-transfer resistance.

Membranes were also characterized by measuring equilibrium water content, and electrical conductance when saturated with PBS. Water content expressed as a percentage of the dry membrane weight ranged monotonically from 2.93 to 8.74 for monomer ratios (S-HEMA to MPTTMS) of 60:40 to 100:0, respectively. Examples of permeability results are given in the following table.

TABLE 1

Permeability of Type 1 Membranes

| Membrane identification | Monomer ratio, S-HEMA to MPTTMS | Permeability to hydroquinone (µA/mM)* | Permeability to oxygen (µA/mM)* | Permeability ratio* | Water content (Wt %) |
|---|---|---|---|---|---|
| C361-1A | 100/0 | 2.94 | 739 | 251 | 8.74 |
| C361-1B | 100/0 | 2.75 | 1413 | 514 | 8.74 |
| C361-2B | 90/10 | 1.07 | 1126 | 1052 | 7.55 |
| C361-3A | 80/20 | 0.87 | 1389 | 1597 | 6.18 |
| C361-3B | 80/20 | 0.90 | 1620 | 1800 | 6.18 |
| C361-4B | 70/30 | 0.39 | 1633 | 4187 | 3.78 |

2.0 mil membrane thickness.
*Determined by extrapolation to infinite electrode rotation rate, 37° C.

As demonstrated by the foregoing data, the mass ratio between the hydrophilic component and the hydrophobic components comprising the second and third polymers can be, for example, between about 50:50 to about 100:0, or more particularly, about 70:30 to about 100:0, including 70:30, 80:20, 90:10, and higher, with ratios of about 90:10 being presently most preferred.

D. Methods of Making Type 2 Membranes of the Invention

Generally, Type 2 membranes are produced by formation of a polymer network from a combination of hydrophobic and masked hydrophilic monomers. The monomers are mixed and polymerized together in a mold, and then the masked hydrophilic polymeric groups are unmasked.

1. Type 2 Membrane-Specific Characteristics.

In this membrane type, the membrane comprises a crosslinked copolymer, IPN, or SIPN. The monomeric precursors for the first and second polymers in a Type 2 membrane may be chosen from those described for the first and second polymers with respect to the Type 1 membrane.

The membrane comprises a hydrophobic component and a hydrophilic component, in addition to the crosslinking component which is present in relatively minor amounts. The hydrophobic component is produced from a hydrophobic monomer, and the hydrophilic component is produced from the use of a masked (e.g., silylated) hydrophilic monomer. The monomers are mixed, and then cross-linked and polymerized together to form, in the preferred embodiments, either a copolymer or an IPN, and then the hydrophilic monomer is unmasked (e.g., desilylated).

The starting materials for the membrane polymers are monomers. Again, the hydrophilic monomer is temporarily masked during polymerization and unmasked after polymerization. For example, a polar group which generates hydrophilicity can be temporarily masked as a hydrophobic group and then converted back to hydrophilic form after polymerization by cleavage of the masking group.

The membrane polymer chains can have varied amounts of hydrophilic and hydrophobic components so that an average amount is present but also a distribution. In some cases, phase separation may occur in a copolymer. For example, some chains may be hydrophilic and phase separate with other hydrophilic chains. Other chains may be hydrophobic and phase separate with other hydrophobic chains.

The amount of the hydrophilic component can be, for example, about 50 mass percent to about 98 mass percent, or more particularly, about 65 mass percent to about 95 mass percent, and more particularly, about 70 mass percent to about 90 mass percent, with respect to the total amount of hydrophilic and hydrophobic component, excluding crosslinker. Preferred ratios of hydrophilic (second) to hydrophobic (first) polymers used are 50:50 to about 95:5, with 87.5:12.5 being presently most preferred.

The amount of crosslinker can be, for example, about 0.1 mass percent to about 10 mass percent, or about 0.5 mass percent to about 5 mass percent, or about 1 mass percent to about 3 mass percent, calculated as grams of crosslinker per total grams of hydrophilic and hydrophobic component.

2. Methods for Production of Type 2 Membranes.

To illustrate synthesis of Type 2 membranes, the practice of a manufacturing method of the invention for their production is exemplified below. The particular approach taken involved polymerizing and cross-linking mixtures composed of the silylated monomer S-HEMA and the monomer MPTTMS between glass plates to form interpenetrating polymers, followed by hydrophilic conversion produced by cleavage of the silyl groups by reference to the following example. Examples of monomer mixtures for use in the method having S-HEMA and MPTTMS as the main components and EGDMA, ESP28, and ESP33 as minor components in specified ratios are shown in Table 2.

TABLE 2

Monomer Composition of Type 2 Membranes

| Membrane Identification | Mixture Components (parts by weight) | | | | | Thickness, mils |
|---|---|---|---|---|---|---|
| | S-HEMA | MPTTMS | EGDMA | ESP28 | ESP33 | |
| E506-2 | 80 | 20 | 2.0 | 1.5 | 1.5 | 1.0 |
| F022-2 | 85 | 15 | 2.0 | 1.5 | 1.5 | 1.0 |
| F023-6 | 90 | 10 | 2.0 | 1.5 | 1.5 | 1.0 |

The mixture was introduced into a membrane mold made from two 4-inch square parallel glass plates separated by a "U"-shaped silicone rubber gasket and held together by clamps. The monomer solution completely filled the mold.

A preferred mold configuration which produces uniformly thin membranes is provided by opposing, smooth-surfaced plates, but other designs can be utilized. Provision should be made to prevent excessive imbibing of atmospheric oxygen in the mold material, since oxygen may interfere with the polymerization process. A preferred mold material is therefore glass, but other materials, including metals and some polymers could also be utilized, either with or without control of the gas atmosphere to which the mold surfaces are exposed before or during polymerization.

The filled glass plate apparatus was baked in an oven at 90° C. for four hours, followed by 110° C. for three hours. After formation, the membrane was retrieved from the mold by disassembly of the mold and soaking of the membrane-attached glass plate in 7% acetic acid overnight, during which the membrane separated from the glass plate. Freed membranes were then attached to an adhesive-backed polyester film frame with multiple openings for support of the membranes during the soaking steps. Frame-mounted membranes were then soaked in the 7% acetic acid solution for nine additional days to complete the desilylation process, followed by soaking in 5% sodium bicarbonate solution to neutralize any residual acetic acid, and soaking in PBS to remove remaining sodium bicarbonate. The mounting frame produced non-wrinkled, evenly-soaked membranes.

For evaluation of permeability, finished membranes were removed from the polyester film frame and mounted over a glucose sensor plate using a five-hole titanium frame and a silicone rubber gasket and secured with nylon fasteners. Each sensor plate was made with an alumina ceramic substrate having multiple independent electrochemical sensor electrode sets, each electrode set having a working, reference, and counter electrode. Sets of electrodes were formed on the plates using thick-film platinum materials. The working and counter electrodes were platinized, and the reference electrode was silver-plated. In each set of electrodes, the working and reference electrodes were circular, with a diameter of 0.005 to 0.007 inches, and the counter electrode was larger, with an equivalent diameter of about 0.020 inches. In each set of electrodes, the working, counter, and reference electrodes were interconnected by an approximately 0.001 inch-thick layer of PBS-saturated PHEMA electrolyte gel, which was overlayed by an approximately 0.002 inch-thick layer of PDMS. All electrodes had individual, insulated conductive tracings that extended to the opposite end of the ceramic substrate and terminated in "pads" for connection to individual electronic potentiostat circuits. Each such circuit polarized its respective working electrode at the cathodic oxygen reduction potential and indicated the resulting current, which relates directly to the oxygen level in the proximity of the electrode. Working electrodes were made sensitive to glucose by locating a layer of immobilized glucose oxidase enzyme 0.005-inch to 0.010-inch thick and 0.075-inch in diameter directly over the PDMS layer overlying the working electrode, with the polymer membrane to be evaluated external to the enzyme layer. The enzyme layer responded to the influx of glucose through the test membrane by catalyzing the consumption of oxygen in its vicinity and the remaining oxygen that diffused to the working electrode produced a glucose-modulated current that was recorded by the electronic potentiostat circuit.

Sensor plates were inserted into a port in a thermostatted reaction vessel containing PBS, maintained at 37° C. such that the sensors were immersed in the solution, and the extended sensor plate was connected electrically to the potentiostat instrumentation. The solution was equilibrated with 5% oxygen in nitrogen and stirred to minimize boundary layers. Aliquots of concentrated glucose solution were systematically added to the reaction vessel so that the resulting concentration ratio of glucose to oxygen ranged from zero to about 45 in units of (mg/dl glucose) per (mmHg oxygen). The resulting glucose-modulated current corresponding to each aliquot was recorded and plots were made of each electrode current, normalized by that electrode's current without glucose, as a function of the glucose-to-oxygen concentration ratio. Examples of such plots are shown in FIG. 1, for three different samples of each of the three membranes listed in Table 2. These plots show linearity of the normalized current with increasing concentration ratio, up to a "break point" or "critical value" (such value dependent on membrane formulation) at which the normalized current is limited by oxygen, and relatively little change at higher values of concentration ratio. For membrane E506-2, which demonstrates a higher oxygen-to-glucose permeability ratio, the breakpoint was estimated by extrapolation of the linear response. For a given membrane, the critical value is useful in estimating the range of sensitivity to glucose that would be obtainable at the oxygen concentration of the implant environment. As an example, linearity of response up to a concentration ratio of 30 would be adequate for indicating glucose concentration of 1050 mg/dl at 35 mmHg of oxygen, and to proportionally lower but acceptable glucose values when the oxygen concentration of the body fluid to which the sensor was exposed was lower. The plots shown in FIG. 1 evidence the outstanding consistency of the permeability properties of these membranes, as well as the predictable nature of the dependence of the membrane permeability properties on membrane polymer formulation. Glucose sensitivity results for these example membranes are summarized in the following table.

TABLE 3

Sensitivity to Glucose-to-Oxygen Concentration Ratio for Type 2 Membranes by Monomer Ratio*

| Membrane Identification | S-HEMA:MPTTMS | Range of linear response to the ratio of glucose to oxygen (mg/dl per mmHg) |
|---|---|---|
| E506-2 | 80:20 | 105 (extrapolated) |
| F022-2 | 85:15 | 42 |
| F023-6 | 90:10 | 22 |

*Minor reactants as in Table 2

A plot was made of the concentration ratio at the break point of concentration linearity, or maximum sensitivity, as a function of S-HEMA content in the membrane formulation. The results indicated that the preferred range of S-HEMA content for useful sensitivity in the body using oxygen-based sensors was 85 to 90%, most preferably about 87.5%. This preferred range of S-HEMA content is based upon methods wherein the desilylation process is carried to completion or near completion. If the desilylation process is abbreviated, then higher contents of S-HEMA would be preferred to provide similar levels of membrane performance.

E. Methods of Making Type 3 Membranes of the Invention

Type 3 membranes are produced by polymerizing together hydrophilic and hydrophobic polymers in an appropriate solvent.

Precursor monomers for first and second polymers in Type 3 membranes are as already described for use in Type 1 and Type 2 membranes. However, unlike the methods for producing Type 1 and Type 2 membranes, polymerization of the monomeric starting materials for Type 3 membranes occurs in a unique solvent system, in which all of the starting monomers and resulting polymers are soluble. Thus, for use in producing Type 3 membranes, the starting hydrophilic monomers need not be masked, or otherwise modified to enhance solubility.

To illustrate synthesis of Type 3 membranes, the practice of a manufacturing method of the invention for their production is exemplified below. The particular approach taken produced Type 3 membranes having intimately associated polymers based on HEMA, MPPMDS and TFEMA in a compatible solvent system.

Mixtures were prepared containing various combinations of HEMA, MPPMDS, MEK, AA, ESP 33, HPMA, TFEMA, and CPT in different amounts, as shown in Table 4. The result of the mixture was a clear solution. The components of the solution were then allowed to react in a sealed vessel at 65° C. in a water bath overnight. The reaction product was poured onto a glass plate, smoothed to uniform thickness, and the solvent allowed to evaporate. Water content was determined by weighing the thus formed membrane before and after soaking in PBS and calculating the water content as a percentage of the membrane dry weight. Measurement of water content was found to be useful in these membranes as a surrogate for direct measurement of membrane permeability.

For use in implantable glucose sensor applications, the preferred range of water content for this type of membrane was found to be 5% to 20%, and the most preferred range was found to be 10% to 20%. In other membrane applications, where the required transport properties for polar and apolar molecules may be different than in implantable glucose sensors, the preferred water content range may be different.

TABLE 5

Sensitivity to Glucose-to-Oxygen Concentration Ratio for a Type 3 Membrane

| Sensor Identification | Membrane Polymer Mixture ID | Water content (% of dry membrane weight) | Range of linear response to the ratio of glucose to oxygen (mg/dl per mmHg) |
|---|---|---|---|
| D431-12-4 | HH | 17.7 | 35 |

F. Glucose Sensor Bodies Including Membranes of the Invention

Any sensor body and sensor design suited to the detection of glucose, such as those employing enzymes in conjunction with the detection of hydrogen peroxide or oxygen, may be utilized in the invention. Examples of sensor designs, including those for sensors suitable for implantation into a body, are described in, for example, Gough, U.S. Pat. No. 6,721,587, the disclosure of which is incorporated herein by this reference to illustrate sensor designs known in the art.

TABLE 4

Combinations of Reactants of Type 3 Membranes and Resulting Water Uptake

| Component | F | G | H | I | T | U | Z | AA | BB | CC | DD | FF | HH |
|---|---|---|---|---|---|---|---|---|---|---|---|---|---|
| HEMA | 2.0 | 2.0 | 1.0 | 1.5 | 0 | 0 | 2.0 | 0 | 0 | 0 | 0 | 2.0 | 2.5 |
| MPPMDS | 3.0 | 3.0 | 3.0 | 3.0 | 3.0 | 2.7 | 2.5 | 2.7 | 2.7 | 2.7 | 2.7 | 2.7 | 2.7 |
| MEK | 5.0 | 5.0 | 5.0 | 5.0 | 5.0 | 5.0 | 5.0 | 5.0 | 5.0 | 4.0 | 0 | 0 | 0 |
| AA | 0.2 | 0.25 | 0.2 | 0.2 | 0.2 | 0.2 | 0.2 | 0 | 0 | 0 | 0 | 0 | 0 |
| ESP33 | 0.1 | 0.1 | 0.1 | 0.1 | 0.5 | 0.5 | 0.5 | 0.5 | 0.5 | 0.5 | 0.5 | 0.5 | 0.5 |
| HPMA | 0 | 0 | 0 | 0 | 2.0 | 2.0 | 0 | 2.0 | 3.0 | 3.0 | 3.0 | 0 | 0 |
| TFEMA | 0 | 0 | 0 | 0 | 0 | 0.3 | 0 | 0.3 | 0.3 | 0.3 | 0.3 | 0.3 | 0.3 |
| CPT | 0 | 0 | 0 | 0 | 0 | 0 | 0 | 0 | 0 | 0 | 4.0 | 4.0 | 4.0 |
| Water content (% of dry membrane weight) | | | | | | | | | | | | | |
|  | 13.5 | 12.0 | 13.2 | 12.1 | 6.1 | 4.4 | 15.3 | 5.9 | 8.4 | 7.4 | 7.1 | 13.9 | 17.7 |

For evaluation of permeability of Type 3 membranes, a sensor plate was constructed as described above, except that instead of applying the membrane in sheet form, external to the immobilized enzyme layer, the Type 3 membrane was applied to the enzyme layer by coating from the solvent solution. Application was accomplished by first drying the immobilized enzyme component, dip coating the component with the membrane solution, allowing the solvent to evaporate from the coating, and then fixing the coated enzyme over the sensor working electrode by means of a mechanical retainer. The sensitivity of the sensor to glucose was determined by placing the sensor in a thermostatted vessel maintained at 37° C. containing phosphate buffered saline, pH 7.3, which was equilibrated with 5% oxygen in nitrogen and stirred. The chronoamperometric glucose-modulated signal was recorded with time as aliquots of concentrated glucose solution were sequentially added to raise the solution glucose concentration from zero to 1468 mg/dl. The results showed a linear sensitivity to glucose up to a characteristic critical value, as with the Type 2 membranes. As an example, the results of testing membrane mixture HH are summarized below.

G. Methods for Evaluation of Membrane Biocompatibility

The membranes of the invention possess long-term biocompatibility. For any particular membrane produced according to the invention, biocompatibility may be assessed by, for example, the following evaluation method.

The method is based on the initial rate of activation of human C3 and C4 immune globulins after in vitro exposure to the implant material, which activation rate provides an indication of the potential in vivo immunogenicity and long-term biocompatibility of the material. The greater the degree of activation, the less biocompatible the material is likely to be in long-term implantation. Membranes of the tested materials were compared to control membranes of medical grade silicone rubber, as well as to immune globulin activation in the absence of material contact. Samples of the materials were incubated in contact with 1 ml of fresh human serum at 37° C. and 25 μl serum aliquots were collected after 0, 2, 5, 15, 30, and 60 minutes of exposure time. Aliquots were placed immediately in 475 μl of sample diluent, and further diluted by 25, 250, and 2500-fold. Diluted samples were then assayed in duplicate for the activated immune globulins as described in Pharmingen Human C3a Elisa Kit #550499 and Human C4a Elisa Kit #5550947.

The results of activated C3 and C4 for specified membranes are reported in Table 6 as a function of exposure time, with comparison to controls.

TABLE 6

Biocompatibility Evaluation by Activation of C3 and C4.

| Exposure time, minutes | D101-3 plus Serum | | D101-6 plus Serum | | Silicone rubber plus Serum | | Serum only | |
|---|---|---|---|---|---|---|---|---|
| | C3a | C4a | C3a | C4a | C3a | C4a | C3a | C4a |
| 0  | 2.40 | 0.15 | 2.40 | 0.15 | 2.40  | 0.15 | 2.40 | 0.15 |
| 2  | 1.66 | 0.12 | 2.17 | 0.13 | 2.62  | 0.16 | 3.06 | 0.18 |
| 5  | 2.23 | 0.15 | 2.05 | 0.14 | 3.67  | 0.21 | 2.53 | 0.19 |
| 15 | 4.23 | 0.19 | 3.57 | 0.18 | 4.96  | 0.29 | 3.20 | 0.21 |
| 30 | 5.36 | 0.22 | 5.24 | 0.21 | 6.93  | 0.34 | 5.05 | 0.28 |
| 60 | 8.91 | 0.30 | 9.13 | 0.28 | 10.22 | 0.48 | 7.43 | 0.36 |

The results show that the sample membrane materials cause only comparable or less activation of C3 and C4, compared to medical grade PDMS and serum only.

H. Production of a Topographically Textured Membrane

Topological features or texturing may be provided on the surface of membranes of the invention to enhance favorable interactions between the implanted membrane and the tissue.

A variety of etching and surface texturing techniques may be employed to produce a textured membrane, either by application of such techniques directly to the membrane, or by application of the techniques to the surfaces of the molds used to produce the membrane. A first technique for production of membranes with controlled surface texture involved the use of a laser-ablation to create small indentations on one side of a polyimide sheet, which was used as one side of a mold used for membrane formation. The monomer solution was then injected into the mold and the procedures described in the preceding examples were employed for membrane formation. Surface features with dimensions in the range of 18 microns to 300 microns were produced using this technique. A second technique involved texturing the surface of glass mold plates by sandblasting the plates with various alumina grits containing particles ranging in size from about 10 microns to about 100 microns and then casting Type 2 membranes using these textured plates. In this manner, membranes were formed with characteristic surface feature sizes ranging from about 5 microns to about 20 microns.

The invention having been fully described, its practice and use are illustrated by the examples below. The examples utilize standard abbreviations throughout, unless otherwise noted. The invention shall be defined solely by the appended claims, and so is not limited by the examples provided.

Example 1

Hydrogen Peroxide-Based Glucose Sensor Constructed with Membrane Operated In Vitro In addition to being useful in oxygen-based enzyme electrode sensors, the membranes of the invention may also find application in hydrogen peroxide-based enzyme electrode sensors, so-called "wired enzyme" sensors, or other implantable sensors. As a demonstration of usefulness in a hydrogen peroxide-based enzyme electrode sensor for glucose, a sensor plate was again constructed using a Type 2 membrane of the invention. The plate construction method was as described above in "Methods for Production of Type 2 Membranes." However, for this demonstration, instead of being poised at a cathodic potential for oxygen reduction, the single working electrode of the sensor plate was poised instead at an anodic potential suited for hydrogen peroxide oxidation, and the PDMS layer overlying the working electrode was removed, to allow diffusion of hydrogen peroxide from the immobilized enzyme layer to the working electrode. The sensor plate was inserted into a port in a thermostatted reaction vessel containing PBS, maintained at 37° C. such that the sensor was immersed in the solution, and the extended sensor plate was connected electrically to the potentiostat instrumentation. The solution was equilibrated with 10% oxygen in nitrogen and stirred to minimize boundary layers. Aliquots of concentrated glucose solution were systematically added to the reaction vessel so that the resulting concentration of glucose ranged from zero to 383 mg/dl. After reaching the peak glucose concentration, the solution was next equilibrated with 5% oxygen in nitrogen to assess the degree of oxygen dependence of the sensor response. The sensor's glucose-dependent electrode current, resulting from hydrogen peroxide oxidation at the working electrode, was recorded throughout the test and is plotted in FIG. 2.

Figure 2:
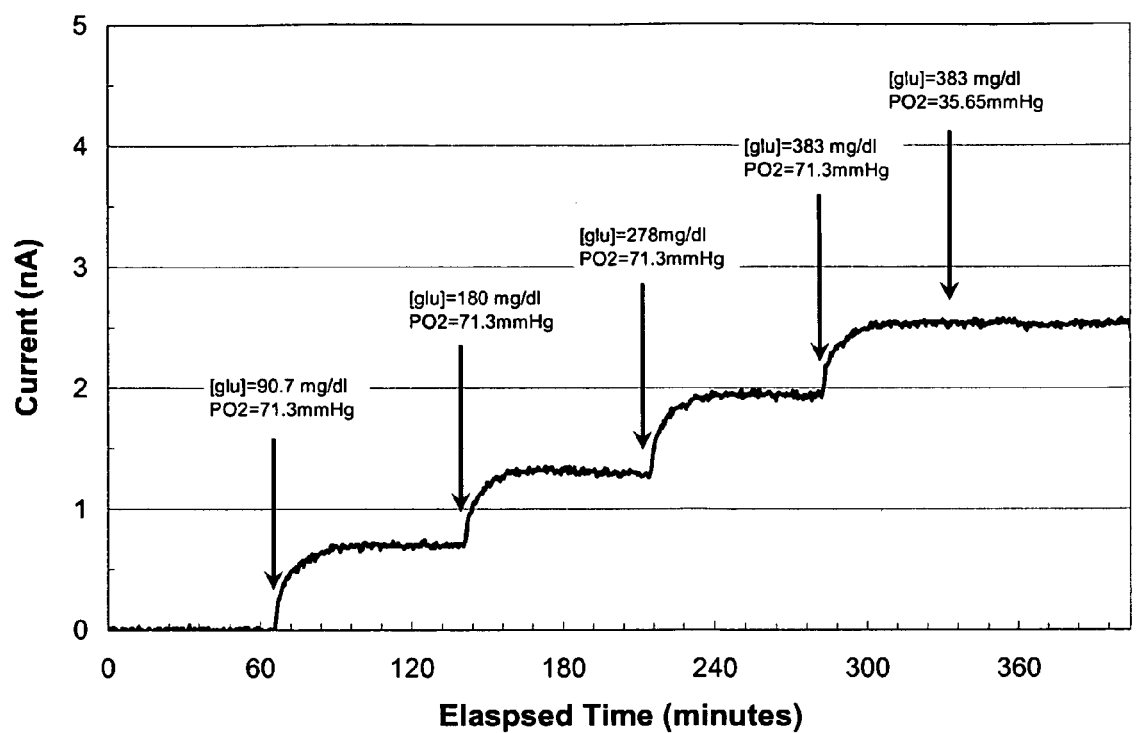
FIG. 2 illustrates a raw signal response obtained in vitro from a glucose sensor based on hydrogen peroxide detection, in which a membrane of the invention is mounted on a sensor body and the sensor is subjected to stepwise changing glucose and oxygen concentrations.

FIG. 2 shows that the sensor's glucose-dependent electrode current increases linearly with increasing glucose concentration, and furthermore that there is no change in the current when the oxygen concentration is reduced by 50%. This result demonstrates that a Type 2 membrane of the invention can provide a sufficiently high permeability ratio of oxygen to glucose to enable linear operation of a hydrogen peroxide-based sensor over the tested regime of oxygen and glucose concentrations.

Example 2

Hydrogen Peroxide-Based Glucose Sensors Constructed with Membranes Operated In Vitro at Low Oxygen Concentration As a further demonstration of usefulness in hydrogen peroxide-based enzyme electrode sensors for glucose, sensor plates were constructed using both Type 1 and Type 2 membranes of the invention. The plate construction method was as described in Example 1, with the addition of a layer of cellulose acetate between the enzyme layer and the underlying electrolyte gel layer, as is understood by those skilled in the art to be useful for reducing the influence of interfering substances. As in Example 1, the working electrodes of the sensor plates were poised at an anodic potential suited for hydrogen peroxide oxidation. The sensor plates were inserted into a port in a thermostatted reaction vessel containing PBS, maintained at 37° C. such that the sensor was immersed in the solution, and the extended sensor plate was connected electrically to the potentiostat instrumentation. The solution was equilibrated with 2% oxygen in nitrogen and stirred to minimize boundary layers. Aliquots of concentrated glucose solution were systematically added to the reaction vessel so that the resulting concentration of glucose ranged from zero to 451 mg/dl. After reaching the peak glucose concentration, the solution was next equilibrated with 1% oxygen in nitrogen to assess the degree of oxygen dependence of the sensor response. The sensors' glucose-dependent electrode currents, resulting from hydrogen peroxide oxidation at the working electrode, were recorded throughout the test and the steady-state values of the currents under the test conditions are summarized in the table below, along with the change in glucose-dependent current due to the change in oxygen content of the equilibrating gas from 2% to 1%. Electrode currents in this test were lower than in Example 1 because of the additional diffusion resistance afforded by the cellulose acetate membrane. As is understood by those skilled in the art, individual sensors can be designed to produce different currents by varying the electrode area as needed.

| Membrane I.D. and Sample Number | Membrane Type | S-HEMA:MPTTMS Ratio | Electrode Current (nA) @ 451 mg/dl | | Signal Change due to Change in Oxygen from |
|---|---|---|---|---|---|
| | | | at 2% oxygen | at 1% oxygen | 2% to 1% (% decrease) |
| C361-3, sample 1 | Type 1 | 70:30 (ratio in imbibing mixture) | 0.298 | 0.296 | 0.67% |
| C361-3, sample 2 | | | 0.247 | 0.245 | 0.81% |
| E491-2, sample 1 | Type 2 | 60:40 | 0.448 | 0.439 | 2.0% |
| E491-2, sample 2 | | | 0.422 | 0.412 | 2.4% |

These results demonstrate that membranes of the invention can provide a sufficiently high permeability ratio of oxygen to glucose to enable substantially oxygen-insensitive operation of hydrogen peroxide-based sensors over physiologically relevant ranges of oxygen and glucose concentrations.

Example 3

Oxygen-Based Glucose Sensor Constructed with Membrane Operated as an Implant in a Hamster This example describes the operation of sensors incorporating a Type 2 membrane and a sensor body as a glucose sensor implant in an experimental hamster preparation.

Male Golden Syrian hamsters obtained from Charles River Laboratories, Cambridge, Mass., weighing between 60 and 200 g were housed in standard micro-isolator cages ventilated with HEPA filtered air and were fed Purina Hamster Chow and water ad libitum. Animals were treated in accordance with NIH guidelines for the care and use of laboratory animals. The window chamber support apparatus, described in detail elsewhere (Milan T. Makale, Joe T. Lin, Richard E. Calou, Amy G. Tsai, Peter C. Chen, and David A. Gough, "Tissue window chamber system for validation of implanted oxygen sensors," Am J Physiol Heart Circ Physiol, June 2003; 284: 2288-2294, incorporated herein by this reference), consisted of two titanium alloy frames, each having a 12 mm diameter circular opening fitted with a ring for attachment of the window or a sensor array.

Each ring extended 0.95 mm toward the tissue and, in conjunction with appropriate spacers to separate the frames, produced sufficient separation to allow vigorous perfusion of the microvasculature in the thin sheet of tissue. One ring had three small pins that penetrated the tissue and mated with holes of the opposing ring to restrict tissue movement. A glass microscope cover slip was secured into the window of one frame and a sensor array disc was secured into the other frame using slotted retaining rings. The frames were held together with four M2-4×10 mm bolts and nuts.

A sensor array comprising three glucose-sensitive oxygen-based working electrodes and ten oxygen-sensitive working electrodes was constructed in the manner described in (Makale, 2003, supra), but with the addition of immobilized enzyme and the subject membrane fixed over three of the working electrodes of the array, in the manner described above for sensor plates in "Methods for Production of Type 2 Membranes."

An individual wire connection was made to each sensor from the back of the array disc. A rectangular ceramic plate having patterned conductive traces mated with a multi-pin fan connector, which was connected via ribbon cables to a custom, multi-channel potentiostat instrument for polarization of the individual working electrodes and production of the signal currents. The data were acquired, displayed, and stored using software written in Labview.

The sensitivity of each sensor was determined individually using a method in which measurements are made in the gas-phase where boundary layers are absent. This method allows repeatable measurement of sensor signals without error due to the possibility of effects from variable mass transfer boundary layers found in the stirred liquid phase. The sensitivity of each sensor was archived respectively and used in calculation of oxygen concentrations. The measurement of oxygen sensitivity was repeated at the end of the study to verify individual sensor stability.

The window chamber plates, bolts, glass coverslips, and sensor arrays were sterilized by soaking for 24 hours in a solution of 6% glutaraldehyde in PBS. The sensors were removed from the solution, rinsed with sterile PBS, and then soaked in sterile PBS with several changes over 48 hrs. All surgical instruments and gauze were sterilized prior to use, and a bead sterilizer was used to resterilize instruments during surgery.

The animals were anesthetized by intraperitoneal injection of 100 mg/kg of ketamine and 250 µg/kg of medetomidine using a 1 ml syringe fitted with a 30 gauge needle. When the animals attained a surgical plane of anesthesia as determined by toe pinch, the fur was shaved from the dorsum. Fine residual hair was removed with a depilatory, and both skin areas were swabbed with Betadine and washed with sterile PBS. The anesthetized animal was placed prone on a heated pad, and the dorsal skin was gently suspended as a longitudinal fold using 4-0 silk secured to vertical metal rods.

After tissues were dissected and the respective tissue-sensor chamber was installed as described below, the animal was injected subcutaneously with 25-75 µg of atipmezole and allowed to recover in a heated enclosure. After a 24-hour recovery, the animal was ready for study. At the conclusion of the experiment, the subject was euthanized with an overdose of pentobarbital (300 mg/kg). Animal subjects were managed according to AALAC guidelines.

For the tissue-fold window chamber, a 12 mm-diameter disc of skin, subcutaneous fat and fascia, and subcutaneous muscle was removed from each side of the skinfold to expose both faces of the folded retractor muscle. Topical broad-spectrum antibiotic cream (polysporin) was applied around the open sites. Approximately 0.4 ml of sterile buffer containing 0.05 ml of a 40 mg/ml solution of a broad-spectrum antibiotic (tobramycin) was deposited dropwise onto the exposed side of the retractor muscle, the titanium frame with the sensor array attached was fitted to one side, and the frame with the glass window was fitted to the opposite side. The plates were then secured in place with bolts and nuts, and a topical antibiotic was applied along the top margin of the skin fold.

Catheters were implanted in the jugular vein and carotid artery of certain animals to facilitate blood sampling and infusion of solutions and pharmacological agents. Catheterization was performed at the same time of chamber implantation in some animals and 24 to 48 hrs after chamber implantation in others. The animal was anesthetized with 100 mg/kg ketamine and 250 µg/kg of medetomidine injected intraperitoneally. The ventral aspect of the neck was shaved, swabbed with Betadine, and washed with saline.

A 2-cm midline incision was made and the right external jugular was exposed using blunt dissection. A sterile, 2 French cannula made of polyurethane tubing with a polished tip containing 100% glycerol USP with 50 units/ml of heparin was introduced into the vein and drawn under the skin to exit dorsally between the shoulder blades. The ventral and dorsal incisions were closed with tissue cement, and the catheter was coiled and secured to the dorsal skinfold chamber frames. The left carotid artery was similarly cannulated in certain animals.

Figure 3:
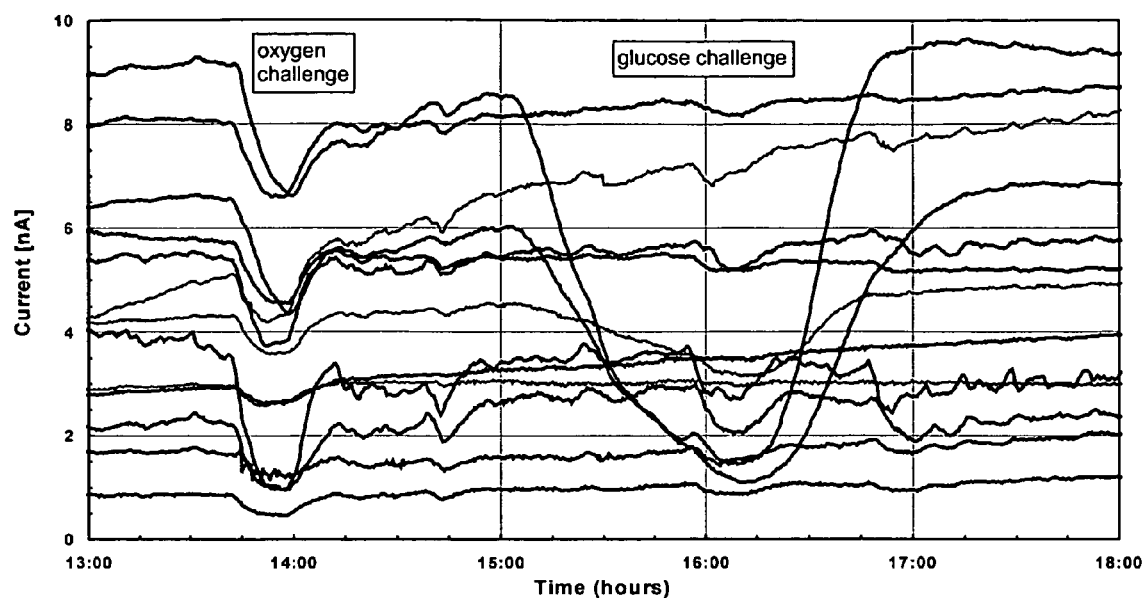
FIG. 3 illustrates a response obtained in vivo in a hamster from an implanted multi-electrode glucose sensor based on oxygen detection, in which a membrane of the invention is mounted on a sensor body.

Simultaneous recordings of electrode currents from three glucose-sensitive and ten oxygen-sensitive elements of the array are shown in FIG. 3 over a 5-hour period on day 4 after implantation. An "oxygen challenge" consisting of a reduction in inspired oxygen levels, and a separate "glucose challenge," consisting of a concentrated glucose infusion into the central circulation are indicated. The three tracings exhibiting the most vigorous response to the glucose challenge are the recordings from the glucose-sensitive elements, while the ten other tracings are the recordings from the oxygen-sensitive elements. The results reflected in FIG. 3 indicate that several phenomena were observed.

First, identical sensors give substantially different signals when implanted due to heterogeneity of the tissue structure.

Second, all sensors respond to the oxygen challenge, but to varying degrees depending on the local tissue environment, and glucose sensors respond vigorously to the glucose challenge, whereas oxygen sensors do not. This demonstrates that the sensor can be sensitive to tissue glucose challenges even in the presence of low tissue oxygen levels, as a result of specification of the membrane permeability ratio. The few oxygen sensors that show slight responses to the glucose challenge reflect small glucose-mediated perfusion effects commonly found in tissues.

Third, the time lag to a glucose concentration challenge is rapid, as glucose sensors show a response within minutes of initiation of the glucose challenge.

Example 4

Oxygen-Based Glucose Sensor Constructed with Membrane Operated as an Implant in a Pig This example describes the operation of sensors incorporating a Type 2 membrane and a sensor body as a glucose sensor implant in an experimental pig preparation.

A Yorkshire pig (6 to 10 weeks of age, 15 to 25 kg) was utilized for the test and was treated in accordance with NIH guidelines for the care and use of laboratory animals. A multi-electrode sensor array was fabricated as described in Example 2, except that the sensor disk was mounted on one aspect of a titanium housing that contained a battery-powered multi-channel potentiostat. A leadwire extending from the opposite aspect of the housing enabled capturing of sensor signals by external instrumentation. Processing of data for conversion of sensor electrode currents into glucose concentration values was performed as described in detail elsewhere (Armour, J. C., J. Y. Lucisano, B. D. McKean, and D. A. Gough, "Application of a Chronic Intravascular Blood Glucose Sensor in Dogs," *Diabetes* 39 (1990), 1519-26), the entire text of which is incorporated herein by this reference.

Animal surgical and sensor testing procedures were as follows: Under anesthesia, a Hickman dual-lumen catheter, modified so that blood sampling could be accomplished through a side port in the catheter several inches upstream from a tip infusion port, was implanted into the jugular vein at the jugular furrow in the neck region of the animal. This central-line catheter was advanced until the tip was at the base of the heart in the precava. The external connections to the catheter were tunneled subcutaneously to the back of the neck of the animal, and served as assay ports for sampling blood glucose during glucose excursion experiments, as well as means to introduce sterile glucose solutions to manipulate blood glucose levels.

A two-inch surgical incision in the skin was made with a scalpel blade followed by blunt dissection to create a pocket between the skin and the underlying muscle. The implant site was located along the dorsal side of the animal about 4 inches from the vertebral line. After inserting the implant, the wound was closed with subcutaneous sutures. The sensor's leadwire was tunneled under the skin and exited the animal about 6 inches from the implant site.

Beginning one week after recovery, the animal was tested with glucose infusions to evaluate sensor performance. The conscious animal was placed in a sling situated next to the data acquisition system. Data were acquired through the percutaneous lead onto a laptop computer, and post-processed for in-depth analyses. Glucose excursion testing included infusion of sterile 50% dextrose solutions through the distal-tip catheter lumen, sampling blood through the proximal side-port catheter lumen, centrifuging the blood samples to provide plasma samples, and measuring the plasma glucose levels with a YSI 2300 STAT Plus glucose analyzer.

Figure 4:
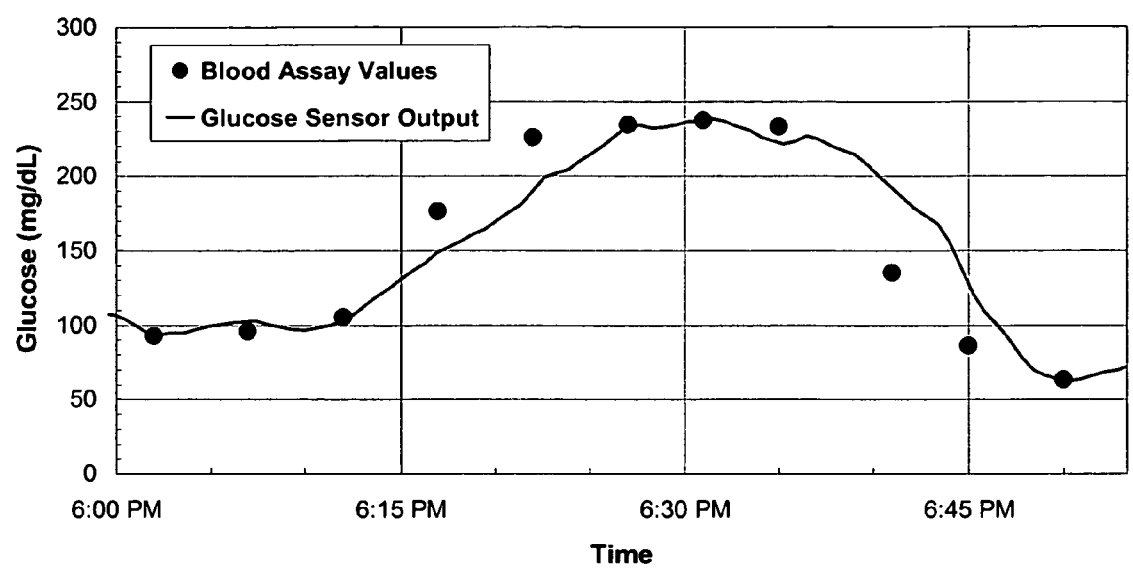
FIG. 4 illustrates a response obtained in vivo in a pig from an implanted glucose sensor based on oxygen detection, in which a membrane of the invention is mounted on a sensor body.

Results from one such glucose excursion test are shown in FIG. 4. During the course of the study, other responsive glucose excursion tests showed similar characteristics. In the figure, glucose concentration calculated from the sensor current is shown as a solid line, and the blood plasma assay values are shown as solid circles. As the plasma glucose level rises from the glucose infusion, the glucose level in the subcutaneous tissue rises and glucose diffuses into the sensor's glucose oxidase region through the membrane. The enzyme reacts with the glucose and consumes oxygen. The glucose-sensitive oxygen electrode registers the change in the oxygen, and exhibits a decrease in sensor current, which is interpreted as a rise in glucose level. Similarly, when the glucose infusion ends, the glucose level in the subcutaneous tissue slowly decreases toward baseline levels. The corresponding glucose-sensitive oxygen electrode current then rises as the glucose (in the glucose oxidase region) is consumed by the enzyme, and not replenished by the now lower concentration of glucose in the environment external to the membrane. In the figure, the rise of the plasma glucose value coincides with the onset of glucose infusion.

The observed lag time of the sensor output with respect to the plasma glucose dynamics is not constant throughout the experiment. During a glucose infusion, plasma glucose levels rise rapidly. As the plasma-dissolved glucose is conveyed through the capillaries supplying the tissue where the implant resides, the interstitial tissue glucose in the region rises rapidly as well. The concentration of glucose external to the enzyme on the glucose electrode is greater than the concentration of glucose inside the enzyme region, and diffusive processes seek to establish a new steady-state of glucose flux through the membrane. When the glucose infusion is stopped, plasma glucose levels drop rapidly in response to high levels of endogenous insulin and the interstitial tissue levels of glucose fall also. During both rising and falling plasma levels, lags may be observed in sensor output, and the lags during falling glucose levels are sometimes greater. The data in this example further demonstrate the suitability of the membrane for use in implanted glucose sensing applications.

The invention having been fully described, its scope is further defined by the appended claims.

What is claimed is:

1. A membrane having controlled permeability to polar and non-polar solutes, for use in an implantable sensor, comprising different first and second polymers, the first polymer comprising at least one crosslinked substantially hydrophobic polymer and the second polymer comprising at least one crosslinked substantially hydrophilic polymer;
   wherein the hydrophobic and hydrophilic polymers are present in a mass ratio from between about 50:50 to 5:95 of the total mass of the hydrophobic and hydrophilic polymers, and form an interpenetrating polymer network, semi-interpenetrating polymer network or polymer blend; and
   wherein further the membrane is characterized by a permeability ratio of oxygen to glucose of about 1 to about 1000 in units of (mg/dl glucose) per (mmHg oxygen).

2. The membrane of claim 1, wherein the hydrophobic and hydrophilic polymers are present in a ratio of 12.5:87.5.

3. The membrane of claim 1, wherein the permeability ratio of oxygen to glucose is about 1 to about 100.

4. The membrane of claim 3, wherein the permeability ratio of oxygen to glucose is about 10 to about 60.

5. The membrane of claim 1, wherein the membrane has a water uptake of about 1 wt. % to about 20 wt. %.

6. The membrane of claim 1, wherein the membrane has a water uptake of about 5 wt. % to about 20 wt. %.

7. The membrane of claim 1, wherein the membrane has a water uptake of about 10 wt. % to about 20 wt. %.

8. The membrane of claim 1, wherein the first polymer comprises a silicone-containing polymer.

9. The membrane of claim 1, wherein the second polymer comprises an acrylate or methacrylate polymer.

10. The membrane of claim 1, wherein the first polymer and the second polymer are not mutually soluble.

11. The membrane of claim 1, wherein the first polymer is prepared from a first monomer, and the second polymer is prepared from a second monomer, and the first and second monomers are not miscible.

12. The membrane of claim 1, wherein the first polymer comprises a silicone-containing polymer, the second polymer comprises an acrylate or methacrylate polymer, and the permeability ratio of oxygen to glucose is about 10 to about 60 in units of (mg/dl glucose) per (mmHg oxygen).

13. The membrane of claim 1, wherein the first polymer comprises a silicone-containing polymer, the second polymer comprises an acrylate or methacrylate polymer, the membrane has a water uptake of about 10 wt. % to about 20 wt. %; and the first polymer and the second polymer are not mutually soluble.

14. The membrane of claim 1, wherein the first polymer is present in units of % wt. of the overall wt. of polymer present in the membrane in a range from 2% wt. to 50% wt.

15. The membrane of claim 14, wherein the first polymer is present in a range from 5% wt to 30% wt.

16. The membrane of claim 15, wherein the first polymer is present in a range from 7% wt to 20% wt.

17. The membrane of claim 1, wherein the second polymer is present in units of % wt. of the overall wt. of polymer present in the membrane in a range from 25% wt to 95% wt.

18. The membrane of claim 17, wherein the second polymer is present in a range from 70% wt to 95% wt.

19. The membrane of claim 18, wherein the second polymer is present in a range from 80% wt to 93% wt.

20. The membrane according to claim 1, wherein the first polymer is selected from the group of polymers consisting of siloxanes, polyphosphazene, and hydrophobically modified celluloses.

21. The membrane according to claim 1, wherein the first polymer includes siloxane linkages in the polymer backbone.

22. The membrane according to claim 21, wherein the first polymer comprises a polyorganosiloxane, poly(dimethyl siloxane), silicone rubber or a silicone elastomer.

23. The membrane according to claim 21, wherein the first polymer is produced from a monomer selected from the group consisting of MPPMDS, MPTTMS, TFEMA and PDMS.

24. The membrane according to claim 1, wherein the second polymer comprises a de-silylated polymer derived from a silylated polymer selected from the group of polymers consisting of silylated vinyl polymers, polyethers, polyesters, polyamides, polyvinyl pyrrolidone, polyvinyl alcohol, glutaraldehyde crosslinked proteins, collagen, albumin, alginates, hydrophilically-modified siloxanes and hydrophilically-modified polypohosphazene.

25. The membrane according to claim 24, wherein the second polymer includes acrylate linkages in the polymer backbone.

26. The membrane according to claim 25, wherein the second polymer is produced from a silylated monomer comprising silylated HEMA or silylated HPMA.

27. The membrane according to claim 1, claim 21 or claim 24 further comprising a cross-linking agent in 0.1 mass % to about 10 mass %, based on grams of cross-linking agent to total grams of polymer.

28. An implantable glucose sensor
   comprising:
   (A) a glucose sensor body; and
   (B) a membrane according to claim 1.

29. An implantable glucose sensor comprising:
   (A) a glucose sensor body;
   (B) at least one membrane disposed on the glucose sensor body comprising a solvent swellable polymeric material comprising hydrophilic polymer component and hydrophobic polymer component;

wherein the hydrophobic and hydrophilic polymers are present in a mass ratio from between about 50:50 to 5:95 of the total mass of the hydrophobic and hydrophilic polymers; and wherein the membrane is characterized by a permeability ratio of oxygen to glucose of about 1 to about 1000 in units of (mg/dl glucose) per (mmHg oxygen).

30. The sensor of claim 29, wherein the hydrophobic and hydrophilic polymers are present in a ratio of 12.5:87.5.

31. An implantable glucose sensor comprising:
(A) a glucose sensor body;
(B) at least one membrane disposed on the glucose sensor body comprising a solvent soluble polymeric material comprising hydrophilic polymer component and hydrophobic polymer component;
wherein the hydrophobic and hydrophilic polymers are present in a mass ratio from between about 50:50 to 5:95 of the total mass of the hydrophobic and hydrophilic polymers; and
wherein the membrane is characterized by a permeability ratio of oxygen to glucose of about 1 to about 1000 in units of (mg/dl glucose) per (mmHg oxygen).

32. The sensor according to claim 31, wherein the permeability ratio of oxygen to glucose is about 10 to about 40.

33. A method of making membranes having controlled permeability to oxygen and glucose, comprising:
(a) providing a hydrophobic polymer membrane, a hydrophobic monomer, and at least one silylated hydrophilic monomer;
(b) combining the hydrophobic and hydrophilic monomers to form a mixture;
(c) impregnating the hydrophobic polymer membrane with the monomer mixture;
(d) polymerizing the monomers; and
(e) desilylating the polymerized hydrophilic monomer,
wherein at least one cross-linking agent is provided separately to each of the monomers in step (a), or to the mixture of monomers in step (b), to form an interpenetrating or semi-interpenetrating polymer network, or polymer blend.

34. The method according to claim 33, wherein the hydrophobic and hydrophilic monomers are immiscible with one another.

35. The method according to claim 33, further comprising disposing the membrane on an implantable sensor body.

36. A method of making membranes having controlled permeability to oxygen and glucose, comprising:
(a) providing a mixture of at least one hydrophobic monomer and at least one silylated hydrophilic monomer;
(b) placing the mixture into a cavity of a membrane mold;
(c) polymerizing the monomers in the mixture; and
(d) desilylating the polymerized hydrophilic monomer,
wherein at least one cross-linking agent is provided to the mixture of monomers in step (a) to form an interpenetrating or semi-interpenetrating polymer network of the monomers, or a polymer blend, or a copolymer.

37. The method according to claim 36, wherein the hydrophobic and hydrophilic monomers are immiscible with one another.

38. A method of making membranes having controlled permeability to oxygen and glucose, comprising:
(a) providing a solution of at least one non-silylated hydrophobic monomer including siloxane linkages in the polymer backbone, at least one non-silylated hydrophilic monomer including acrylate linkages in the polymer backbone, at least one polymerization initiator and a solvent compatible with the hydrophobic and hydrophilic monomers, wherein none of the monomers present in the solution is silylated, and wherein further, the hydrophobic monomer and the hydrophilic monomer are present in a mass ratio from between about 50:50 to 5:95 of the total mass of the hydrophobic and hydrophilic monomers;
(b) allowing the monomers in the solution to polymerize; and
(c) allowing the solvent to evaporate.

39. A method for making an implantable glucose sensor comprising mounting at least one membrane according to claim 1, claim 21 or claim 24 on a biocompatible sensor body.

40. A membrane with controlled permeability to apolar and polar solutes produced by the method of claim 33.

41. A membrane with controlled permeability to apolar and polar solutes produced by the method of claim 36.

42. A membrane with controlled permeability to apolar and polar solutes produced by the method of claim 38.

* * * * *